United States Patent
Singh et al.

(10) Patent No.: US 6,448,097 B1
(45) Date of Patent: Sep. 10, 2002

(54) MEASURE FLUORESCENCE FROM CHEMICAL RELEASED DURING TRIM ETCH

(75) Inventors: Bhanwar Singh, Morgan Hill; Bharath Rangarajan, Santa Clara; Ramkumar Subramanian, Sunnyvale, all of CA (US)

(73) Assignee: Advanced Micro Devices Inc., Sunnyvale, CA (US)

( * ) Notice: Subject to any disclaimer, the term of this patent is extended or adjusted under 35 U.S.C. 154(b) by 0 days.

(21) Appl. No.: 09/911,236

(22) Filed: Jul. 23, 2001

(51) Int. Cl.[7] ............ H01L 31/26; H01L 21/66; G03C 5/00
(52) U.S. Cl. ............ 438/16; 250/492.22; 430/313
(58) Field of Search ............ 250/492.2, 492.22; 430/305–325; 438/16

(56) References Cited

U.S. PATENT DOCUMENTS

| | | | |
|---|---|---|---|
| 5,742,658 A | 4/1998 | Tiffin et al. | 378/44 |
| 6,177,233 B1 * | 1/2001 | Uesawa | 430/290 |
| 6,238,487 B1 | 5/2001 | Jenkins et al. | 134/2 |
| 6,369,887 B2 * | 4/2002 | Eyolfson et al. | 250/458.1 |

FOREIGN PATENT DOCUMENTS

| | | | | |
|---|---|---|---|---|
| JP | 402069640 A | * | 3/1990 | 250/206.2 |
| JP | 405036795 A | * | 2/1993 | 356/237.1 |
| JP | 200146853 A | * | 5/2000 | H01J/9/14 |

OTHER PUBLICATIONS

U.S. patent application Publication, U.S. 2001/0013930, Eyolfson et al., Published Aug. 16, 2001, filed Apr. 25, 2001.*

* cited by examiner

*Primary Examiner*—Olik Chaudhuri
*Assistant Examiner*—Timothy Sutton
(74) *Attorney, Agent, or Firm*—Amin & Turocy, LLP (57) ABSTRACT

A system and method is provided for determining and controlling development of a semiconductor substrate employing fluorescence spectroscopy. One aspect of the invention relates to a system and method employing fluorescence spectroscopy to facilitate control of a chemical trim etch process during development of a photoresist material layer. The chemical trim etch process comprises applying a trim compound or material to a patterned photoresist. The trim compound or material is diffusable into the sides and top of the patterned resist. The diffused regions of the resist are soluble in a developer, which facilitates creating smaller features in the patterned photoresist. The fluorescence spectroscopy system can be employed to measure isolated and dense gratings or CDs and use the evolution of the CD to determine when to terminate the chemical trim process.

28 Claims, 9 Drawing Sheets

MEASURE FLUORESCENCE FROM CHEMICAL RELEASED DURING TRIM ETCH

FIELD OF THE INVENTION

The present invention generally relates to semiconductor processing, and in particular to a system and method for monitoring and controlling of a chemical trim process to improve critical dimension (CD) control based on fluorescence spectroscopy analysis.

BACKGROUND OF THE INVENTION

In the semiconductor industry, there is a continuing trend toward higher device densities. To achieve these high densities there has been and continues to be efforts toward scaling down the device dimensions on semiconductor wafers. In order to accomplish such high device packing density, smaller and smaller features sizes are required. This includes the width and spacing of interconnecting lines and the surface geometry such as corners and edges of various features. Since numerous interconnecting lines are typically present on a semiconductor wafer, the trend toward higher device densities is a notable concern.

The requirement of small features (and close spacing between adjacent features) requires high resolution photolithographic processes. In general, lithography refers to processes for pattern transfer between various media. It is a technique used for integrated circuit fabrication in which a silicon slice, the wafer, is coated uniformly with a radiation-sensitive film, the resist, and an exposing source (such as optical light, X-rays, or an electron beam) illuminates selected areas of the surface through an intervening master template, the photomask, for a particular pattern. The lithographic coating is generally a radiation-sensitized coating suitable for receiving a projected image of the subject pattern. Once the image is projected, it is indelibly formed in the coating. The projected image may be either a negative or a positive of the subject pattern. Exposure of the coating through the photomask causes a chemical transformation in the exposed areas of the coating thereby making the image area either more or less soluble (depending on the coating) in a particular solvent developer. The more soluble areas are removed in the developing process to leave the pattern image in the coating as less soluble polymer.

Projection lithography is a powerful and essential tool for microelectronics processing. However, lithography is not without limitations. Patterning features having dimensions of about 0.25 μm or less with acceptable resolution is difficult at best, and impossible in some circumstances. Patterning small features with a high degree of critical dimension control is also very difficult. Procedures that increase resolution, improved critical dimension control, and provide small features are therefore desired.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

A system and method is provided for determining and controlling development of a semiconductor substrate employing fluorescence spectroscopy. One aspect of the invention relates to a system and method employing fluorescence spectroscopy to facilitate control of a chemical trim etch process during development of a photoresist material layer. The chemical trim etch process comprises applying a trim compound or material to a patterned photoresist. The trim compound can be a gas or a solution. The trim compound or material is diffusable into the sides and top of the patterned resist. The diffused regions of the resist are soluble in a developer, which facilitates creating smaller features in the patterned photoresist. The fluorescence spectroscopy system can be employed to measure isolated and dense gratings or CDs and use the evolution of the CD to determine when to terminate the chemical trim process.

In one aspect of the invention, a signature library is provided containing a plurality of signatures corresponding to various CD measurements. A measurement signal provided by a fluorescence spectroscopy system can be converted into an actual CD measurement corresponding to a CD of one or more resist structures or features on a patterned photoresist material layer. A signature is then generated corresponding to the actual CD measurement and matched with a signature in the signature library. A trimming compound application process is then repeated and signatures matched until the appropriate match is made corresponding to the desired CD.

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention will become apparent from the following detailed description of the invention when considered in conjunction with the drawings.

DETAILED DESCRIPTION OF THE INVENTION

The present invention will now be described with reference to the drawings. The present invention will be described with reference to a system and method for determining and controlling development of a semiconductor substrate employing fluorescence spectroscopy. One aspect of the invention relates to a system and method employing fluorescence spectroscopy to facilitate control of a chemical trim etch process during development of a photoresist material layer. The chemical trim etch process comprises applying a trim compound or material to a patterned photoresist. The trim compound or material can be a gas or a solution. The trim compound or material includes a particular acid or base component that is diffusable into the sides and top of the patterned resist. The diffused regions of the resist are soluble in a developer, which facilitates creating smaller features in the patterned photoresist, which in turn facilitates creating smaller features in a layer under the patterned photoresist layer. A fluorescence spectroscopy system can be employed to measure isolated and dense gratings or CDs and use the evolution of the CD to determine when to terminate the chemical trim process.

For example, the particular trimming component can contain a cleaving compound that causes a chemical interaction to take place within the portions of the resist adjacent the trimming component, forming a thin deprotected resist layer within the resist. The cleaving compound from the trimming component diffuses into a thin portion of the resist adjacent the coating. The cleaving compounds at or near the interface of the trimming compound and the resist cause a chemical change wherein labile groups of the resist polymer are cleaved or deprotected and the cleaved or deprotected portions of the resist become removable by an appropriate solvent or developer. That is, the cleaving compound cleaves labile moieties of the resist material, thereby changing the solubility characteristics of the thin portion of the resist material wherein such cleavage takes place. Thus, a thin deprotected resist layer is formed within the developed resist which is then removable or further developable after or while the coating is removed.

The present invention also utilizes the natural fluorescence of the photoresist material since the photoresist material is an organic material to determine and control the above-mentioned process. The detection and quantification of specific substances by fluorescence emission spectroscopy are founded upon the proportionality between the amount of emitted light and the amount of a fluorescent substance present. When energy in the form of light, including ultra violet and visible light, is directed at an organic material, fluorescent substances therein will absorb the energy and then emit that energy as light having a longer wavelength than the absorbed light. A fluorescing molecule absorbs a photon resulting in the promotion of an electron from the ground energy state to an excited state. When the electron's excited state relaxes from a higher energy vibrationally-excited state to the lowest energy vibrationally-excited state, energy is lost in the form of heat. When the electron relaxes to the ground electronic state, light is emitted at a lower energy than that absorbed due to the heat-energy loss, and hence at a longer wavelength than the absorption. The amount of emitted light is determined by a photodetector.

In practice, the light is directed into a sample cell through an optical light filter so that the light transmitted is of a known wavelength, which is referred to as the excitation wavelength. The sample cell is designed to optimize the fluorescence response depending on the analysis method chosen. The emitted light is similarly screened through a filter so that the amount of emitted light is measured at a known wavelength or a spectrum of wavelengths, which is referred to as the emission wavelength. When the measurement of the fluorescence intensity of specific substances or categories of substances at low concentrations is desired or required, the filters are set for a specific combination of excitation and emission wavelengths, selected for substantially optimum low-level measurements.

A variety of fluorescence analysis techniques can be applied alone or in combination in accordance with the present invention. The fluorescence analysis techniques can include techniques that measure and/or indicate the appearance or disappearance of fluorescence, a shift in excitation and/or emission wavelengths of fluorescence, fluorescence changes based on specific light absorbance changes, a well-defined temperature-dependency of fluorescence, a well-defined pH-dependency or other water condition dependency of fluorescence, and the exploitation of a temperature-dependency and/or pH-dependency of fluorescence to see or enhance one or more of the above techniques.

Figure 1:
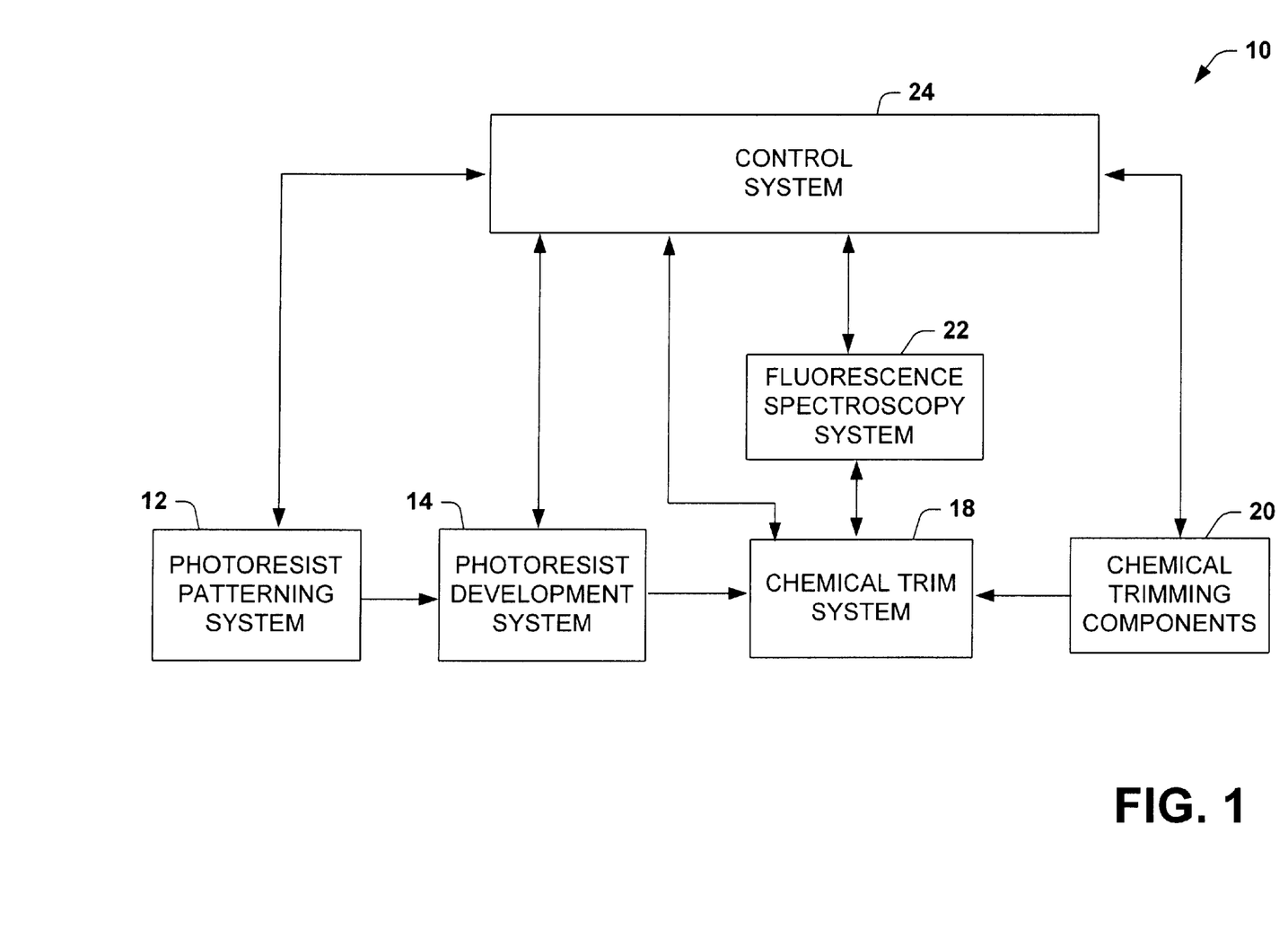
FIG. 1 is a block representation of a system in accordance with one aspect of the present invention.

FIG. 1 illustrates schematic block diagram of a portion of a development system 10 for facilitating development of a semiconductor device utilizing a chemical trim etch system to improve CD controls. The system 10 employs a fluorescence spectroscopy system to monitor the evolution of one or more CDs to determine when to end the chemical trim etch process. It is to be appreciated that many additional stages and processes are typically employed during the development of a semiconductor wafer. The system 10 comprises a photoresist application and patterning system 12 coupled to a photoresist development system 14. The photoresist application and patterning system 12 applies a photoresist material layer on top of a layer to be patterned (e.g., polysilicon, oxide, metal) overlaying a substrate. For example, the resist can contain a polymer having an acid labile group that reacts with a trimming compound such as a cleaving compound to form an acidic substance that is removable by a base developer.

The substrate is typically a silicon substrate optionally with various elements and/or layers thereover, including metal layers, barrier layers, dielectric layers, device structures, active elements and passive elements including polysilicon gates, wordlines, source regions, drain regions, bit lines, bases, emitters, collectors, conductive lines, conductive plugs, etc. The photoresist application and patterning system 12 also exposes the photoresist to a pattern using a stepper system or the like during the step of patterning the photoresist layer with a desired circuit pattern.

The substrate with the patterned photoresist is then moved to the photoresist development system 14 via a track or the like for developing the patterned photoresist. A developer is applied to the patterned photoresist layer using a nozzle to apply the developer. The developer removes selectively irradiated or non-irradiated portion of the photoresist. A washing or cleansing solution then rinses the excess developer from the substrate. The substrate is then moved to a chemical trim system 18 for controllably decreasing the size of the developed resist structures. It is to be appreciated that the photoresist patterning system 12 and the photoresist development system 14 can be integrated into a single system.

The chemical trim system 18 applies a trimming compound (e.g., acidic solution, acidic gas, basic solution, basic gas) that diffuses into the top and side portions of the resist structures. The trimming compounds make a portion of the patterned photoresist (e.g., sides and top portions of resist structures) soluble to a developer, for example, which facilitates creating smaller features in the patterned photoresist, which in turn facilitates creating smaller features in an underlying layer (e.g., an oxide layer) under the patterned photoresist. The trim rate is generally proportional to the formulae of the trimming compound, referred to as the chemical trimming components 20, the concentration of the trimming compound, the volume of the trimming compound, the vapor pressure inside a trim chamber and/or the temperature inside the trim chamber. The chemical trim system 18 also includes a developer system for applying a developer to the patterned photoresist. The developer is applied to the patterned photoresist layer using a nozzle to apply the developer. The developer removes portions of the photoresist in which the trimming compound has diffused (e.g., top and side portions of resist features).

A fluorescence spectroscopy system 20 is employed to detect one or more CDs after the development process has been complete. The fluorescence spectroscopy system 20 can differentiate between an isolated grating or CD and a dense grating or CD and utilize this information in providing a desired measurement. The CD measurement or pattern is then transmitted to the control system 24, which matches the measurement or pattern with an expected measurement or pattern. If the fluorescence spectroscopy system 22 and the control system 24 determine that the desired CD has not been obtained, the control system 24 repeats the application of the trimming compound and the developer until the appropriate CD is obtained. The control system 24 is also adapted to adjust the chemical trimming components 20 (e.g., concentration, volume, pressure, temperature) relating to providing trimming compound to the patterned photoresist. The chemical trim system 18 employs the changed parameters in real-time, for the next substrate or repeats the development process for the current substrate being worked on (e.g., in-situ). Additionally, the changed parameters can be transmitted to other systems for compensating for the defects or providing for improvements associated with the photoresist development process.

It is to be appreciated that the fluorescence spectroscopy system 20 can be operably connected to one or more of process to provide feedback/feedforward information concerning the development of the patterned photoresist material layer. Such feedback/feedforward information can be employed to determine when to end one or more processes. Additionally, the feedback/feedforward information can be provided to adjust parameters associated with previous and/or subsequent processes within and outside the system 10.

Figure 2:
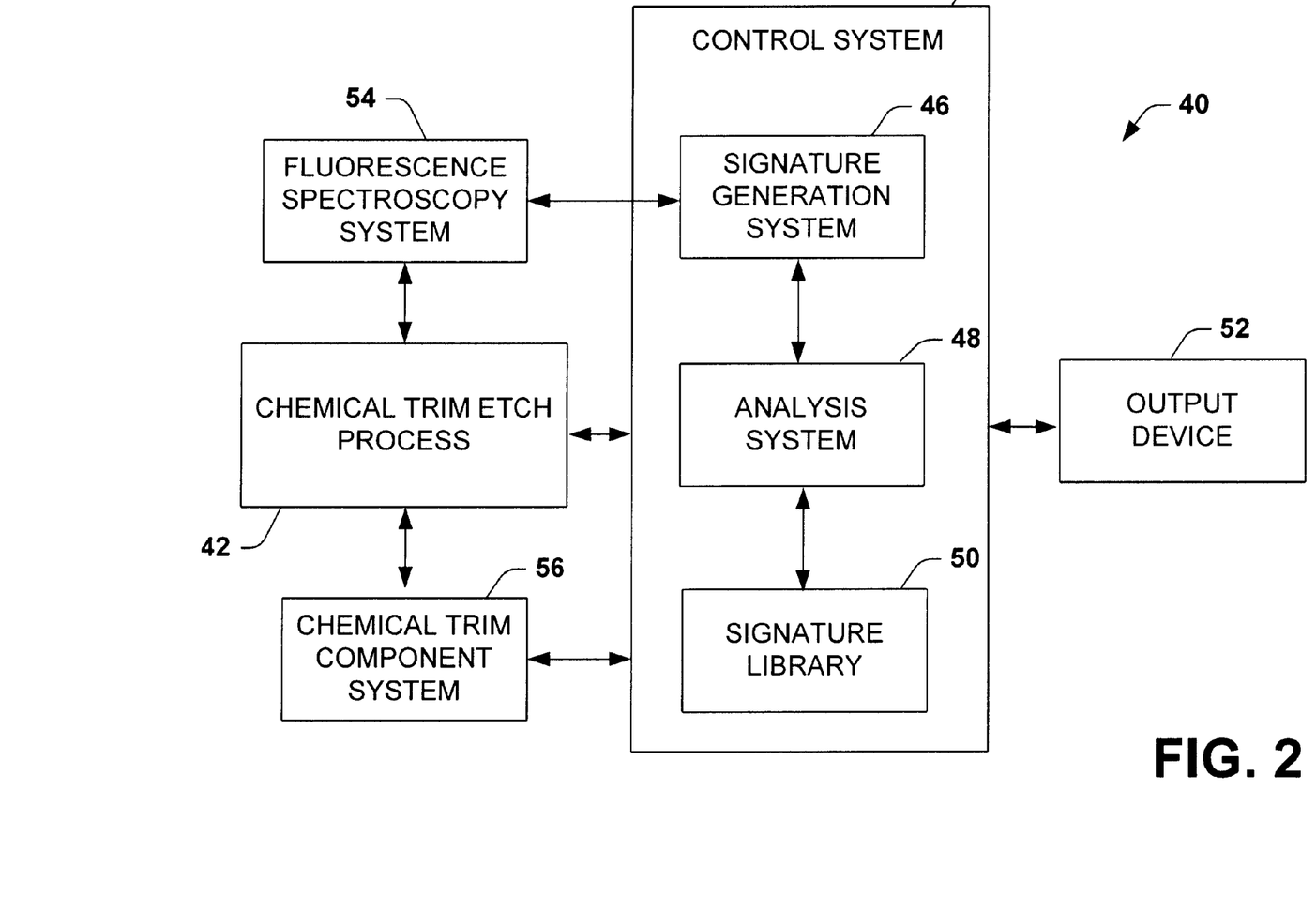
FIG. 2 is a block representation of a system in accordance with another aspect of the present invention.

FIG. 2 illustrates a system 40 for in-situ monitoring of a chemical trim etch process schematically indicated at 42. The process 42, for example, includes applying a trimming compound to a patterned photoresist, waiting a predetermined time for the trimming compound to diffuse into the side and top portions of resist features of the patterned photoresist and applying a developer to the patterned photoresist to remove the diffused portions of the patterned photoresist. The system 40 also includes a control system 44 for controlling operating characteristics of the process 42. The operating characteristics associated with the process 42 may include, for example, trimming compound deposition and/or developer deposition enablement, the temperature of the environment, the temperature of the trimming compound and developer, concentration of trimming compound and developer, chamber and applications pressures associated with the process, and timing parameters associated with different steps in a multi-step fabrication process. The control system 44 may adjust one or more selected operating parameters of the process based on sensed operating conditions associated with the process 42.

A fluorescence spectroscopy system 54 is operatively associated with the process 42 to measure in-situ one or more CDs of the patterned photoresist after completion of one or more chemical trim etch steps. A portion of the fluorescence spectroscopy system 54 can be in an enclosed processing chamber. The fluorescence spectroscopy system 54, for example, samples one or more CDs being formed on the substrate at one or more locations, such as near the center and near one or more edge locations of the substrate. In particular, it may be desirable to obtain measurements from two or more spaced apart locations, such as at the center and one or more edge positions. Such measurements may enable a better determination as to uniformity of the desired CDs, which in accordance with an aspect of the present invention, may be employed to adjust the fabrication process to achieve a desired level of uniformity of desired CDs. The fluorescence spectroscopy system 54 may implement any known technique operable to measure the CDs being formed in the process 42. Alternatively, Ultra-Violet/Violet spectroscopy can be employed to carry out the present invention.

By way of further illustration, fluorescence spectroscopy may be employed to extract information about CDs which an incident light has been directed and a light beam has been emitted proportional to the fluorescence of the photoresist material present on the substrate. One or more gratings may be located on a substrate. Such gratings may be formed on the substrate, for example, at the same stage in fabrication when alignment markers are formed thereon. Light emitted from the one or more gratings and/or features is collected by one or more photodetector components of the fluorescence spectroscopy system 54. It is to be appreciated that any suitable UltraViolet/Violet spectroscopy system may be employed to carry out the present invention, and such systems are intended to fall within the scope of the claims.

The fluorescence spectroscopy system 54 is coupled to the control system 44 for providing a signal indicative of the one or more CDs being formed in the process 42. The control system 44, for example, includes memory (not shown) for storing target CDs, which may vary according to the process. The control system 44 also includes a signature generation system 46, which creates a signature from the signal measurements over a CD thickness or width range that is employed to determine the evolution of the CD during repeated chemical trim etch processes. The control system 44 also includes a signature library 50 that includes hundreds of thousands of signatures, each corresponding to a particular CD measurement. The control system 44 is coupled to a chemical trim component system 56 and adapted to communicate changes to parameters (e.g. concentration, volume, pressure, temperature, diffusion time), provided by the chemical trimming component system 56 to the process 42, relating to providing trimming compound and developer to the patterned photoresist.

An analysis system 48 is provided for comparing the generated signature with signatures in the signature library 50. By examining a signature library 50 of CD thickness and/or width signatures, a determination can be made at what point the one or more CDs have met a desired criteria. The control system 44 is coupled to the process 42 and may be programmed and/or configured to compare the measured CD relative to a target and determine what action (if any) should be taken to drive the process 42, so that a target CD and/or a desired level of CD may be achieved. Once a desired result is obtained, the control system can terminate the process 42 and provide an indication thereof. The control system 44 is also coupled to an output device 52, so that results can be displayed to a user.

Figure 3:
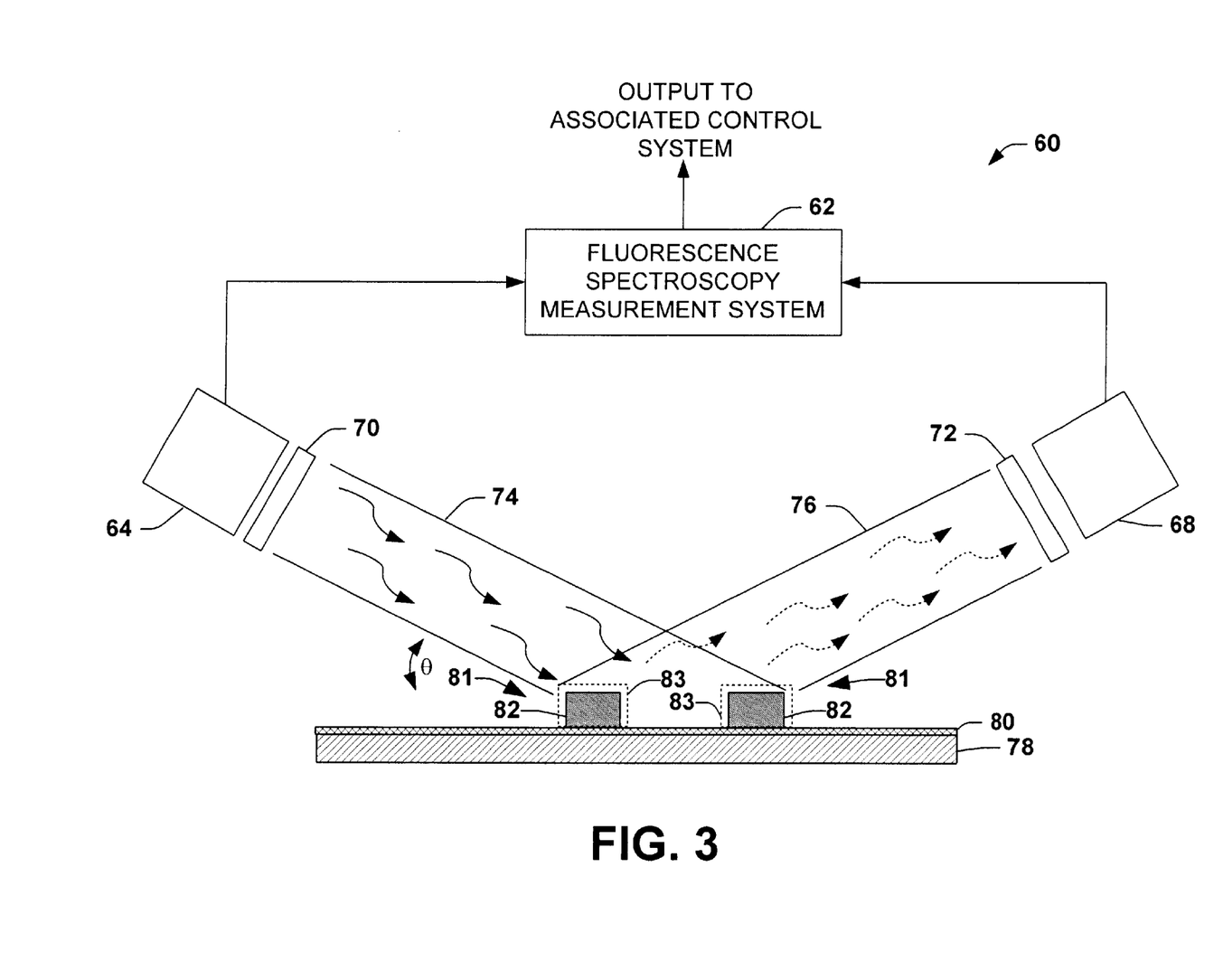
FIG. 3 is a block diagram illustrating an example of a measurement system employing fluorescence spectroscopy that may be utilized in accordance with one aspect of the present invention.

FIG. 3 illustrates an example of a fluorescence spectroscopy system 60 that may be implemented, in accordance with an aspect of the present invention, to measure the one or more CDs of a patterned photoresist material over an underlying layer 80. The fluorescence spectroscopy system 60 includes a measurement system 62 coupled to a light source 64 and a photodetector 68. The light source 64 is a broadband light source, such as a Xe Arc lamp or the like. The light source 64 produces a spectrum of polychromatic and/or monochromatic light over a predetermined wavelength range of interest (e.g., 100–800 nm). A light beam 74 enters an optional filter 70 so that the amount of emitted light is measured at a known wavelength or a spectrum of wavelengths. The azimuth angle of the light beam is at a known angle θ relative to the plane of incidence defined by the propagation direction of the beam and the normal N to the exposed surface of the underlying layer.

The fluorescence of the photoresist present on the underlying layer 80 results in an emitted light beam 76 proportional to the amount of photoresist present. The emitted light beam 76 will then pass through an optional screening filter 72 to the photodetector 68. The beam 76 then enters the detector 68 which measure the intensity of the different wavelengths of light through the wavelength range of interest that pass through the filter 72. The detector 68 or the measurement system 62 then determines, for example, a CD of a structure such as a line or a width between two lines based on the measurement. As illustrated in FIG. 3, the underlying layer 80 (e.g., an oxide) resides over a substrate 78. A pair of resist line structures 81 have been formed over the underlying layer 80. Prior to a chemical trim etch process, the pair of resist line structures consisted of the structures 83 illustrated in phantom. After the chemical trim etch process, the pair of resist line structures consist of structures 82. The fluorescence spectroscopy system 60 then can perform a CD measurement such as the thickness of one or more of the resist line structures 81 or the width between the resist line structures to determine if a desired CD has been acheived. If the desired results are not achieved, the chemical trim etch process can be repeated and one or more parameters can be adjusted, until the desired results are achieved.

Figure 4:
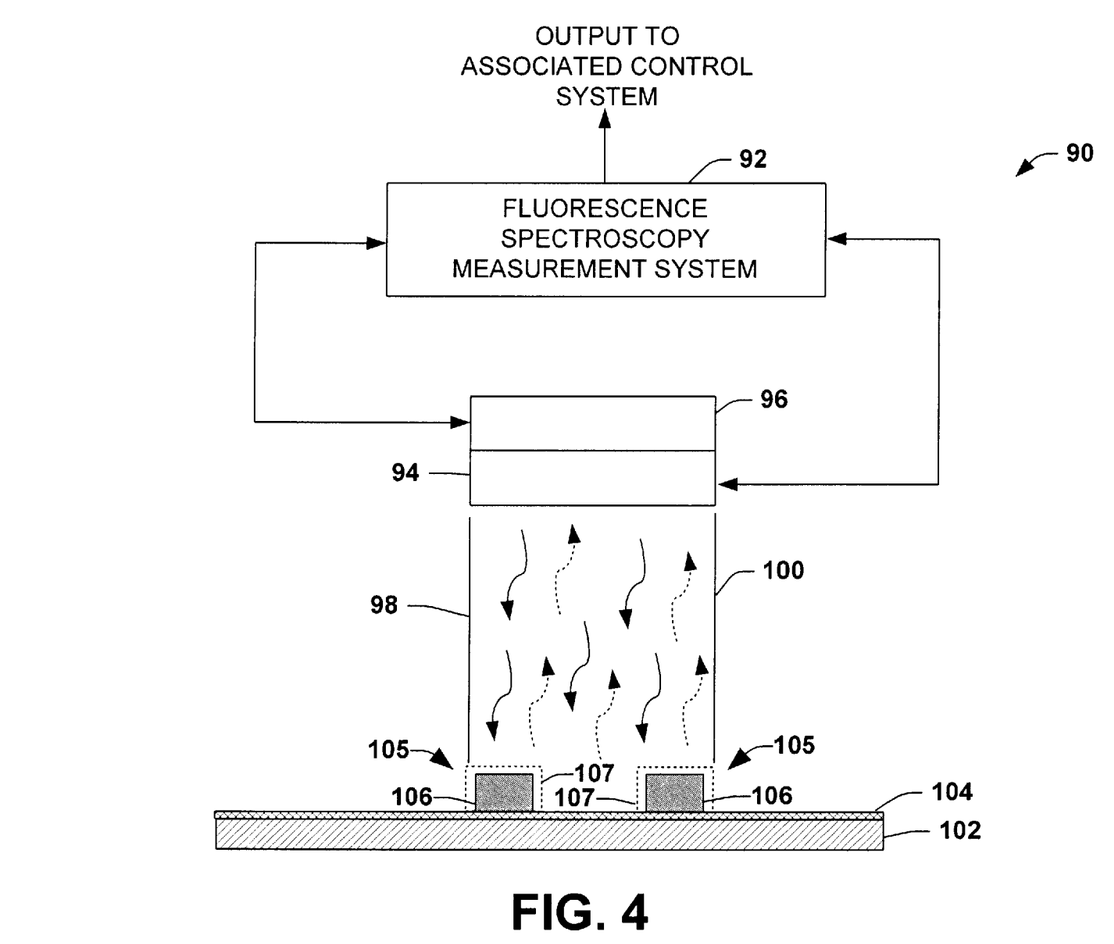
FIG. 4 is a block diagram illustrating an example of a measurement system employing fluorescence spectroscopy that may be utilized in accordance with another aspect of the present invention.

FIG. 4 illustrates an example of a fluorescence spectroscopy system 90 that may be employed to derive an indication of a CD of a patterned resist structure. In the fluorescence spectroscopy technique of FIG. 4, a light source 94 emits a beam of light 98 that is supplied at a fixed incident angle (e.g., about 90 degrees) relative to an underlying layer 104. The fluorescence spectroscopy system 90 includes a measurement system 92 coupled to the light source 94 and a photodetector 96. The light source 94 can be a broadband light source, such as a Xe Arc lamp or the like. The light source 94 produces a spectrum of polychromatic and/or monochromatic light over a predetermined wavelength range of interest (e.g., 100–800 nm).

The fluorescence of the photoresist present on the underlying layer 104 results in an emitted light beam 100 proportional to the amount of photoresist present. The emitted light beam then enters the detector 96 which measures the intensity of the different wavelengths of light through the wavelength range of interest. The detector 98 or the measurement system 92 then determines, for example, a CD of a resist structure such as a line or a width between two lines based on the measurement. As illustrated in FIG. 4, the underlying layer 104 (e.g., an oxide) resides over a substrate 102. A pair of resist line structures 105 have been formed over the underlying layer 104. Prior to a chemical trim etch process, the pair of resist line structures consisted of the structures 107 illustrated in phantom. After the chemical trim etch process, the pair of resist line structures consist of structures 106. The fluorescence spectroscopy system 90 then can perform a CD measurement such as the thickness of one or more of the resist line structures 105 or the width between the resist line structures. If the desired results are not achieved, the chemical trim etch process can be repeated and one or more parameters can be adjusted, until the desired results are achieved.

Figure 5:
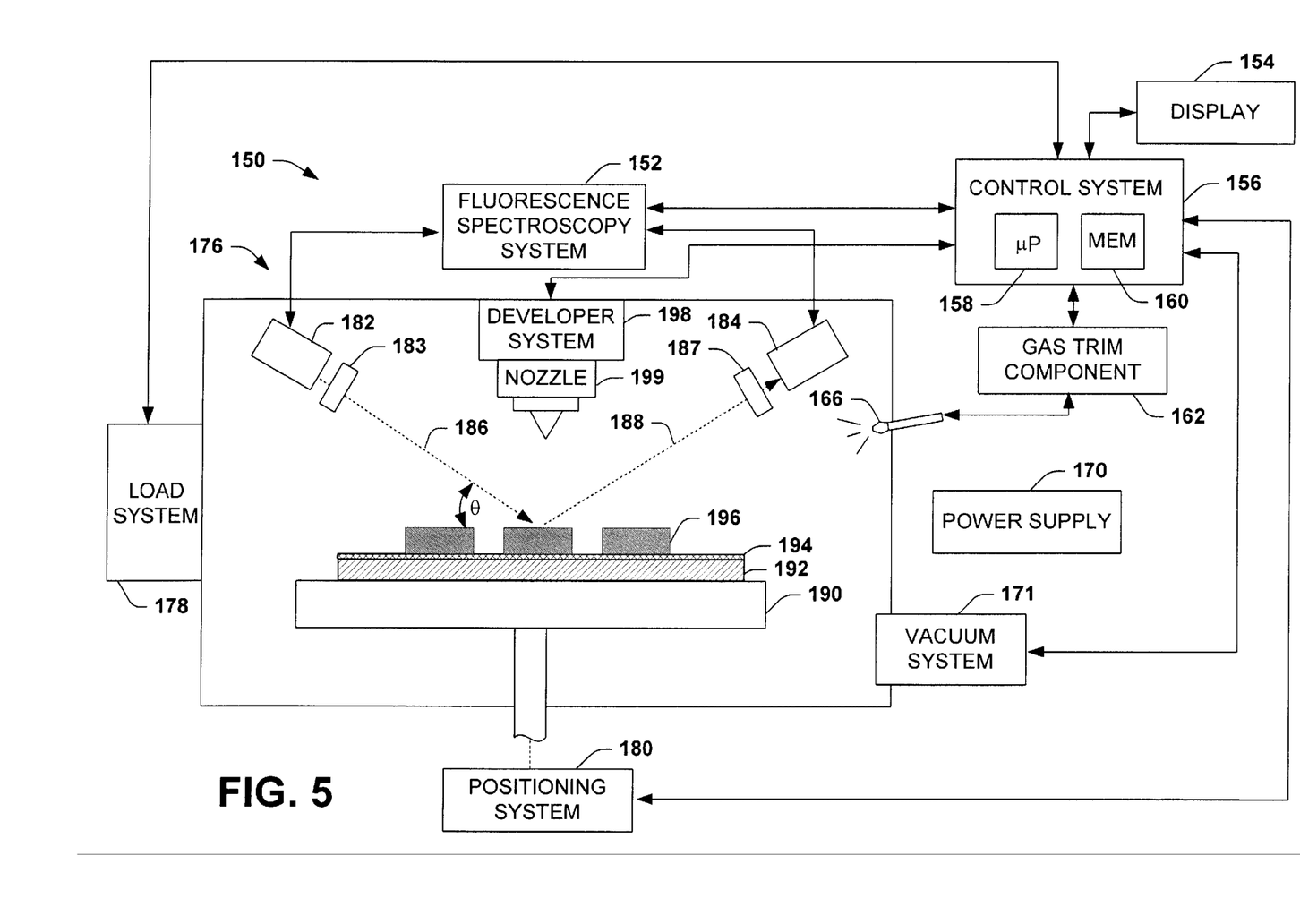
FIG. 5 is a functional block diagram of a chemical trim etch system in accordance with one aspect of the present invention.

FIG. 5 illustrates a system 150 having a fluorescence spectroscopy system 152 for controlling a CD associated with a resist structure in a patterned photoresist layer in accordance with an aspect of the present invention. In the present example, a gaseous phase chemical trim process is employed. However, it is to be appreciated that the gas trim component system 162 can be replaced by a trimming solution component system, which can apply a trimming solution to the patterned photoresist utilizing a nozzle or the like.

In the example of FIG. 5, a patterned resist is exposed to a gas containing a cleaving compound. While the resist is in contact with the gas containing a cleaving compound, a chemical interaction takes place within the portions of the resist adjacent the gas, forming a thin deprotected resist layer within the resist. The cleaving compound from the gas diffuses into a thin portion of the resist adjacent the coating. The cleaving compounds at or near the interface of the gas and the resist cause a chemical change wherein labile groups of the resist polymer are cleaved or deprotected and the cleaved or deprotected portions of the resist become removable by an appropriate solvent or developer. That is, the cleaving compound cleaves labile moieties of the resist material, thereby changing the solubility characteristics of the thin portion of the resist material wherein such cleavage takes place. Thus, a thin deprotected resist layer is formed within the developed resist which is then removable or further developable after or while the coating is removed.

For example, an acid containing gas is introduced into a reaction chamber via the gas trim component system 162 where a patterned acid catalyzed resist 196 is located. While the resist is in contact with the acid containing gas, a chemical interaction takes place within the portions of the resist adjacent the acid containing gas forming a thin deprotected resist layer within the resist. The hydronium ions or protons from the acid containing gas diffuse into a thin portion of the resist adjacent the acid containing gas. The hydronium ions or protons at or near the interface of the acid containing gas and the resist polymer cause a chemical change wherein the deprotected portions of the resist become removable by an appropriate developer. That is, hydronium ions or protons cleave acid labile moieties of the resist material, such as t-butoxycarbonyl moieties from a resist polymer backbone, thereby change the solubility characteristics of that portion of the resist material. Thus, a thin deprotected resist layer is formed within the developed resist which is then removable after or while the acid containing gas is removed.

A fluorescence spectroscopy system 152 is then employed to measure one or more CDs of resist structures associated with the patterned and trim etched photoresist 196. The width of lines may be analyzed to determine whether acceptable critical dimensions have been achieved. Other parameters including, but not limited to horizontal trim rate, vertical trim rate and trim-rate percent uniformity may also be analyzed.

Referring again to FIG. 5, the system 150 includes a process chamber 176 that includes a support, such as a stage 190 (or chuck) operative to support a substrate 192, such as a wafer. A positioning system 180 is operatively connected to the support 190 for positioning the stage 190 at a desired position within the chamber 176.

The gas trim component system 162 is operably coupled to the chamber 176 for selectively providing gaseous trim compound into the chamber to form a film layer on the photoresist patterned layer 196 and the underling layer 194. The gas trim component system 162 includes a source of a gaseous medium (a vapor) containing a cleaving compound to be formed on the patterned photoresist material layer 196. The gas is provided into the chamber through a conduit that terminates in a nozzle, indicated at 166. A developer system 198 is provided in the chamber 176. The developer system is adapted to apply a developer via a nozzle 199 to the patterned photoresist 196 after the patterned photoresist 196 has been exposed to the gas trim compound. The developer removes portions of the photoresist in which the trim compound has diffused (e.g., sides and top portions of resist structures). A vacuum system 171 is provided to remove the gas trimming compound, the excess developer and the removed diffused resist portions. If a trimming solution is employed, the vacuum can be adapted to remove the excess trimming solution.

The system 150 also may include a load system 178 operatively connected to the chamber 176 for loading and unloading substrates (e.g., wafers) into and out of the processing chamber. The load system 178 typically is automated to load and unload the wafers into the chamber at a controlled rate.

The fluorescence spectroscopy system 152 includes a light source 182 and a photodetector 184. The light source 182 produces a spectrum of polychromatic and/or monochromatic light over a predetermined wavelength range of interest (e.g., 100–800 nm). A light beam 186 enters an optional filter 183 so that the amount of emitted light is measured at a known wavelength or a spectrum of wavelengths. The azimuth angle of the light beam is at a known angle θ relative to the plane of incidence defined by the propagation direction of the beam and the normal N to the exposed surface of the underlying layer.

The fluorescence of the photoresist pattern 196 on the underlying layer 194 results in an emitted light beam 188 proportional to the amount of photoresist present. The emitted light beam 188 will then pass through an optional screening filter 187 to the photodetector 184. The beam then enters the detector 184 which measure the intensity of the different wavelengths of light through the wavelength range of interest that pass through the filter 187. The fluorescence spectroscopy system 152 will then transmit this information to a control system 156. The control system 156 will determine one or more CDs associated with resist structures, for example, a CD of a structure such as a line or a width between two lines based on the measurement. The control system 156 will then compare the one or more CDs with desired CDs. If the desired results are not achieved, the chemical trim etch process can be repeated and one or more parameters can be adjusted, until the desired results are achieved.

The control system 156 includes a processor 158, such as a microprocessor or CPU, coupled to a memory 156. The processor 158 receives measured data from the fluorescence spectroscopy system 152. The processor 158 also is operatively coupled to the gas trim component system 162, the developer system 198, the vacuum system 170, the position system 180 and the load station 178. The control system 156 is programmed/and or configured to control and operate the various components within the processing system 150 in order to carry out the various functions described herein.

The control system 156 is also adapted to adjust the gas trimming parameters (e.g, concentration, volume, pressure, temperature) relating to providing trimming compound to the patterned photoresist 196. The gas trim component system 162 employs the changed parameters in real-time, for the next substrate or repeats the development process for the current substrate being worked on (e.g., in-situ). Additionally, the control system 156 is also adapted to adjust the parameters associated with application of developer to the patterned photoresist 196 (e.g., concentration, volume, pressure, temperature).

The memory 160 may include read only memory (ROM) and random access memory (RAM). The ROM contains among other code the Basic Input-Output System (BIOS) which controls the basic hardware operations of the system 150. The RAM is the main memory into which the operating system and application programs are loaded. The memory 160 also serves as a storage medium for temporarily storing information such as temperature, temperature tables, position coordinate tables, fluorescence spectroscopy information, thickness tables, CD measurements, CD signatures and algorithms that may be employed in carrying out the present invention. The memory 160 also can hold patterns against which observed data can be compared as well as information concerning grating sizes, grating shapes, fluorescence spectroscopy information, achieved profiles, desired profiles and other data that may be employed in carrying out the present invention. For mass data storage, the memory 160 may include a hard disk drive.

A power supply 170 provides operating power to the system 150. The system further may include a display 154 operatively coupled to the control system 156 for displaying a representation (e.g., graphical and/or text) of one or more process conditions, such as CD dimensions, temperature, concentrations, gas flow rates, etc. The display 154 further may show a graphical and/or textual representation of the measured optical properties at various locations along the surface of the substrate.

Figure 6:
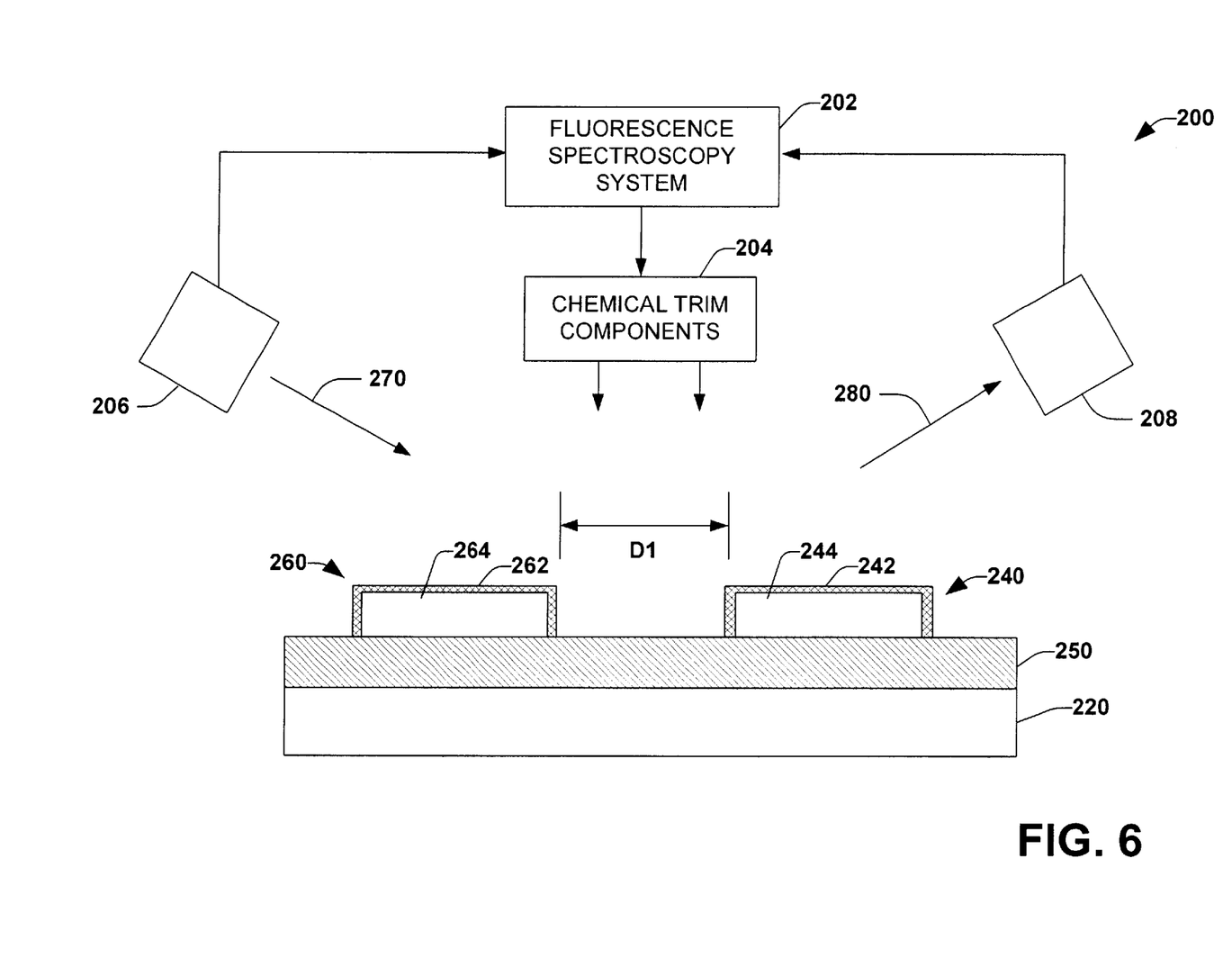
FIG. 6 is a cross-sectional view of a photoresist layer on a wafer being trimmed and monitored in accordance with an aspect of the present invention.

Turning now to FIG. 6, a fluorescence spectroscopy system 200 is illustrated directing a light 270 at a substrate 220 and receiving back an emitted light 280. The fluorescence spectroscopy system 200 may include one or more components that are located inside a trim chamber and/or one or more components that are not located inside a trim chamber. The emitted light beam 280 will be affected by the fluorescence of the photoresist material residing on the substrate 220, the size, shape and location of resist features on the substrate 220 and the size, shape and location of spaces between such features. By way of illustration, a gap D1 between a first resist feature 260 and a second resist feature 240 is illustrated. The first and second resist features are illustrated as residing over an oxide layer 250 on top of the wafer 220. One or more chemical trimming components 204 are illustrated operatively connected to the fluorescence spectroscopy system 200. The chemical trimming components 204 can be one or more of a variety of trim components as parameters associated with introducing a chemical trim etch into a reaction chamber, control process temperature, and the like, which in turn facilitates more precisely removing patterned photoresist. Thus, portions of the patterned photoresist structures 260 and 240 may be removed as a result of chemical trim process associated with the trimming components 204 and the trimming compound.

FIG. 6 illustrates a pair of resist structures after undergoing a chemical trim etch process in which a chemical trim compound creates diffused regions 262 and 242 and non-diffused regions 264 and 244 in the structures 260 and 240, respectively. A gap D1 can be measured by the fluorescence spectroscopy system 200 to determine whether desired CDs have been achieved on the substrate 220. For example, a signature associated with the gap D1 may indicate that further trimming of the structures 240 and 260 may be required. Such trimming may require, for example, additional chemical trimming compound, a different temperature, a different pressure and/or a change of formula. Thus, information operable to control the gas trim components 204 may be generated by the fluorescence spectroscopy system 200.

As trimming of the patterned photoresist structures 240 and 260 progresses, light emitted from the photoresist structures 240 and 260 may produce various signatures. The sequence in which such signatures are generated can be employed to determine the rate at which trimming is progressing. Similarly, the sequence of such signatures may be employed to determine the rate at which the gap D1 is changing. Such changes in rates can be employed to determine completion times, for example, and thus can be employed to facilitate scheduling subsequent chemical trim processes.

By way of illustration, at a first point in time T1, light emitted from the photoresist structures 240 and 260 may produce a signature S1 that indicates that the gap D1 has reached a first measurement. Similarly, at a second point in time T2, light emitted from the photoresist structures 240 and 260 may produce a signature S2 that indicates that the gap D1 has reached a second measurement and at a third point in time T3, emitted from the photoresist structures 240 and 260 may produce a signature S3 that indicates that the gap D1 has reached a third desired measurement, and that trimming should conclude. Analyzing the sequence of signatures, and the time required to produce transitions between such signatures can facilitate determining whether trimming is progressing at an acceptable rate. Feedback information can be generated from such sequence analysis to maintain, increase and/or decrease the rate at which trimming progresses by, for example, manipulating gas formulae, trim chamber temperature, etc.

Figure 7:
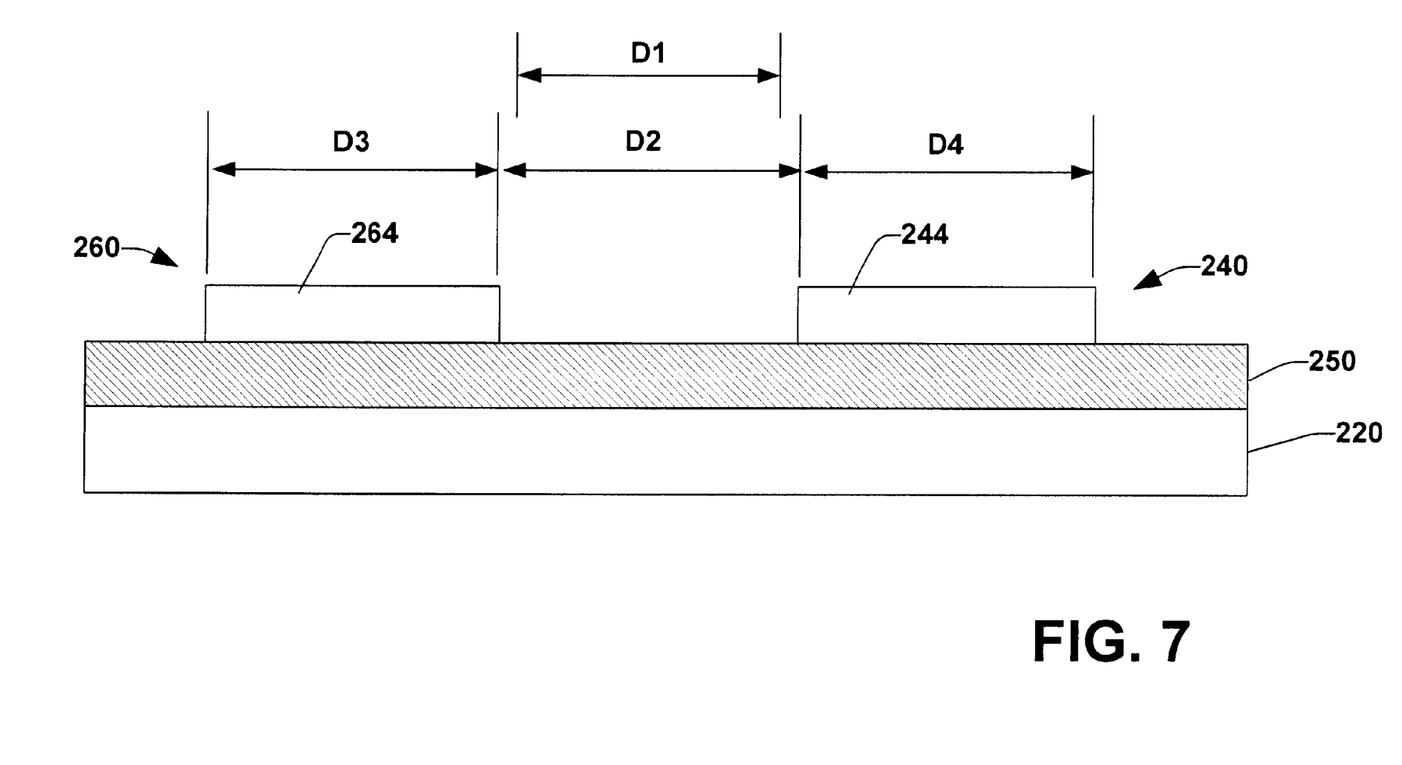
FIG. 7 is a cross-sectional view of a wafer being monitored for CDs in accordance with an aspect of the present invention.

Turning now to FIG. 7, measurements that may affect signatures generated by a fluorescence spectroscopy system associated with controlling one or more chemical trim processes to facilitate achieving desired critical dimensions are illustrated. Controlling such measurements (e.g., gate width and thickness, linewidth and thickness) can be important to reliable and efficient operation of an integrated circuit. FIG. 7 illustrates the CDs associated with the resist structures 260 and 240 after removal of the diffused regions 262 and 242 of FIG. 6. The diffused regions can be removed by a developer or the like. The developer can be a base when the diffused regions contain an acid or an acid when the diffused region contain a base.

A desired critical dimension for the distance between the resist structures 260 and 240 may be the distance D2. For example, a gap of size D2 may be required to facilitate fabricating a subsequent feature that will reside between the features 260 and 240. Lithography may have occurred at an earlier point in time, but the lithography may have produced the structures 260 and 240 in such a manner that they will not produce the desired CD (e.g., gap size D2). Thus, a trimming compound can be applied to the structures 260 and 240, in an attempt to reduce the size of the patterned photoresist structure to widths D3 and D4, which would then allow the gap size D1 to be increased to the gap size D2.

Thus, the present invention facilitates generating information concerning the distances D1, D2, D3 and D4 and the resulting topographies of the resist. Such information, generated, at least in part, in response to in-situ emitted light being analyzed by fluorescence spectroscopy techniques can be employed to provide real-time feed-forward information that can be employed to control chemical trim processes so that desired critical dimensions can be achieved, thus providing advantages over conventional systems.

Figure 8:
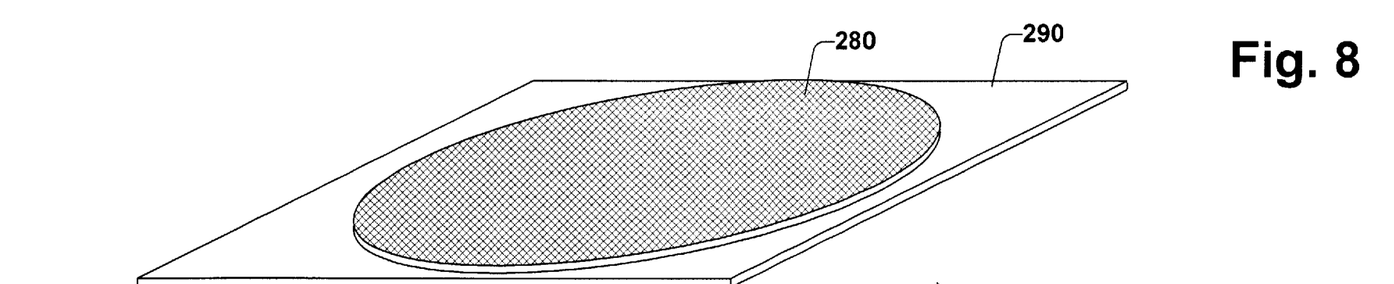
FIG. 8 is a perspective illustration of a wafer upon which a photoresist that may be trimmed is located in accordance with an aspect of the present invention.

FIG. 8 illustrates a perspective view of a chuck 290 supporting the wafer 280, whereupon one or more gratings may be formed. The wafer 280 may be divided into a grid pattern as shown in FIG. 8. Each grid block (XY) of the grid pattern corresponds to a particular portion of the wafer 280, and each grid block is associated with one or more gratings and/or one or more portions of one or more gratings. The grid blocks are individually monitored for chemical trim process parameters and trimming may be individually controlled for each grid block. It is to be appreciated that the size and/or shape of gratings can be manipulated to facilitate analyzing different critical dimensions. For example, for a particular layer in an integrated circuit, a CD relating to a width between features may be important. Thus, the gratings can be patterned to optimize analyzing the width between features.

Figure 9:
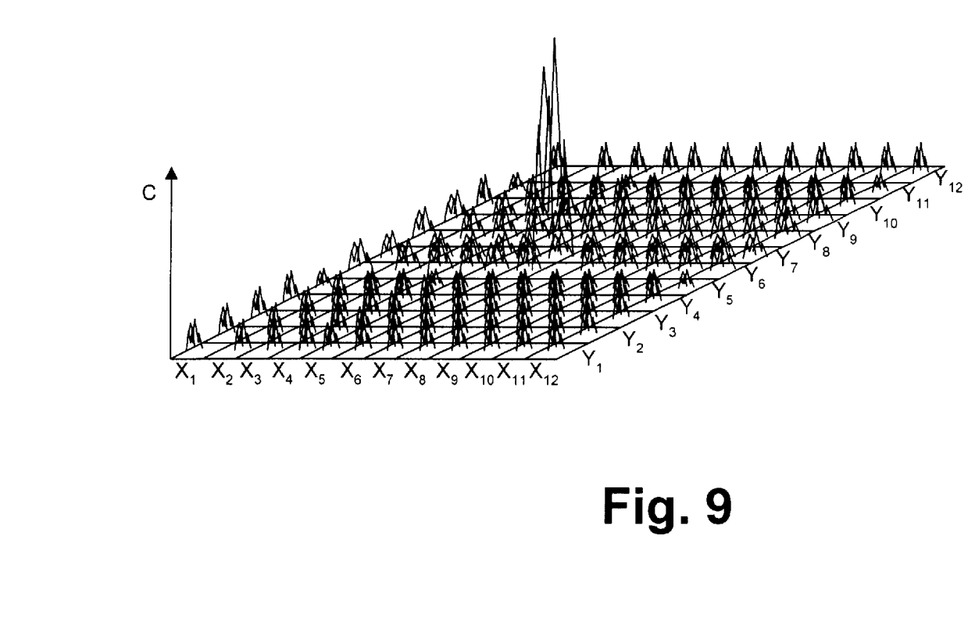
FIG. 9 is a representative three-dimensional grid map of a wafer illustrating CD measurements taken in accordance with an aspect of the present invention.

In FIG. 9, one or more gratings in the respective portions of the wafer 280 ($X_1Y_1 \ldots X_{12}, Y_{12}$) are monitored for CDs produced during the chemical trim process using emitted light, the fluorescence spectroscopy system 22 (FIG. 1) and the control system 24 (FIG. 1). Exemplary CD measurements produced during trimming for each grating are shown. As can be seen, the CD measurement at coordinate $X_7Y_6$ is substantially higher than the CD measurement of the other portions XY. It is to be appreciated that the wafer 280 may be mapped into any suitable number of grid blocks, and any suitable number of gratings may be formed on the wafer 280. Although the present invention is described with respect to one chemical trimming component corresponding to one grid block XY, it is to be appreciated that any suitable number of chemical trimming components corresponding to any suitable number of wafer portions/grid blocks may be employed.

Figure 10:
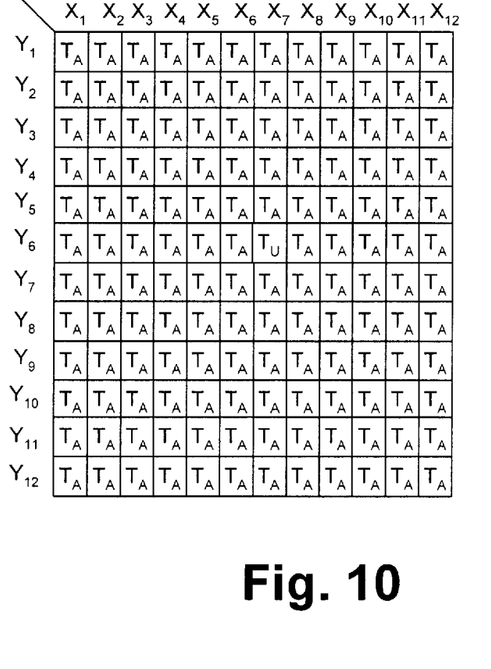
FIG. 10 is a trimming measurement table correlating the CD measurements of FIG. 9 with desired values for the CDs in accordance with an aspect of the present invention.

FIG. 10 is a representative table of CD measurements taken for the various grid blocks that have been correlated with acceptable CD values for the portions of the wafer 280 mapped by the respective grid blocks. As can be seen, all the grid blocks, except grid block $X_7Y_6$, have CD measurements corresponding to an acceptable CD table value ($T_A$) (e.g., are within an expected range of trimming measurements), while grid block $X_7Y_6$ has an undesired CD table value ($T_U$). Thus, the control system 24 has determined that an undesirable trimming condition exists at the portion of the wafer 280 mapped by grid block $X_7Y_6$. Accordingly, the control system 24 can drive at least a chemical trimming component 20$_{7,6}$, which corresponds to the portion of the wafer 280 mapped at grid block $X_7Y_6$, to attempt to produce an acceptable CD. It is to be appreciated that the chemical trimming components 20 may be driven so as to maintain, increase, and/or decrease, the rate of trimming of the respective portions of the wafer 290 as desired.

In one example of the present invention, the chemical trimming component 280 associated with grid block $X_7Y_6$ may change the temperature associated with the grid block and/or the concentration of the active ingredients of a cleaving compound (e.g., acid, base, organic compound) associated with the grid block. When the control system 24 determines that the trimming process has reached a predetermined threshold level, the control system 24 may terminate the trimming by one or more chemical trimming components 20, thus enabling more precise control of the trimming process, which provides advantages over conventional systems.

Figure 11:
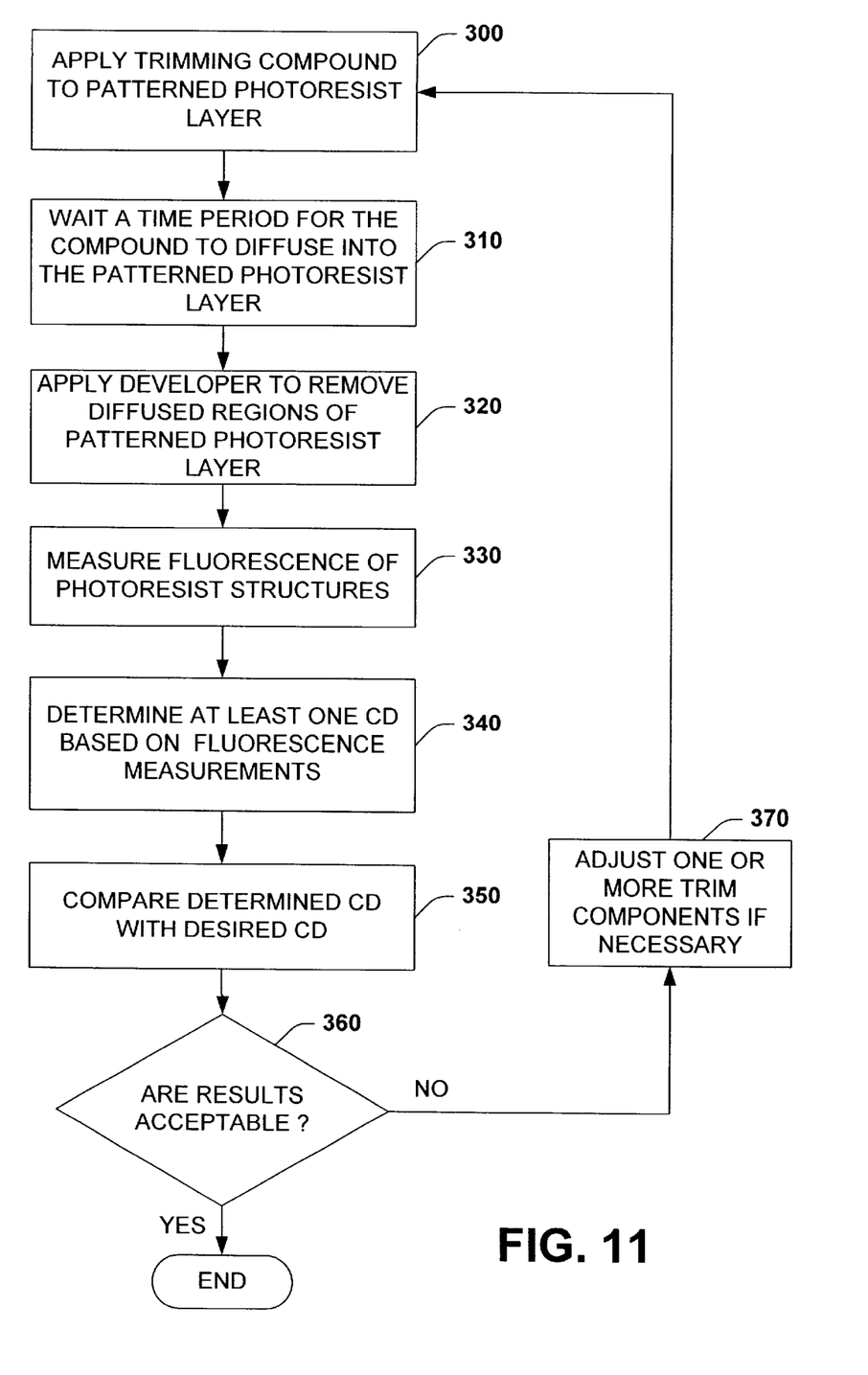
FIG. 11 is a flow diagram illustrating a methodology for a chemical trim process in accordance with an aspect of the present invention.

In view of the exemplary systems shown and described above, a methodology, which may be implemented in accordance with the present invention, will be better appreciated with reference to the flow diagram of FIG. 11. While, for purposes of simplicity of explanation, the methodology of FIG. 11 is shown and described as executing serially, it is to be understood and appreciated that the present invention is not limited by the illustrated order, as some blocks may, in accordance with the present invention, occur in different orders and/or concurrently with other blocks from that shown and described herein. Moreover, not all illustrated blocks may be required to implement a methodology in accordance with the present invention.

Turning now to FIG. 11, the methodology begins at 300 in which a trimming compound is applied to a patterned photoresist layer. The trimming compound, for example, can contain a cleaving compound that causes a chemical interaction to take place within the portions of the resist adjacent the trimming component, forming a thin deprotected resist layer within the resist that can be removed by a developer. The trimming compound can be a gas or a solution. The methodology then waits a time period for the trimming compound to diffuse into the patterned photoresist layer at 310. The process then proceeds to 320. At 320, a developer is applied to the patterned photoresist layer to remove the diffused regions of the patterned photoresist layer, so that CDs of photoresist structures can be reduced.

From 320, the process proceeds to 330 in which the fluorescence of one or more photoresist structures is measured. The measured fluorescence is employed to determine at least one CD of the remaining photoresist structures at 340. For example, certain sample critical dimensions can be measured during the trimming of the photoresist structures to determine if the trimming has been completed. The determined CD is then compared with an desired CD at 350. For example, one or more CDs can be compared with signatures corresponding to measurements of the CDs at particular trim processing intervals as described in FIGS. 2 and 6–7. At 360, the method determines if the results are acceptable. If the results are not acceptable (NO), the method proceeds to adjust one or more trim components (e.g., concentration, volume, pressure, temperature, diffusion time) if necessary at 370 and returns to 300 to repeat the trimming process. If the results are acceptable (YES), the methodology ends.

What has been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A semiconductor processing system, comprising:
   a processing chamber operable to provide a trimming compound to a patterned photoresist material layer disposed on a substrate located in the chamber, the trimming compound diffusing into top and side portions of the patterned photoresist material layer to formed diffused regions;
   a developer system operable to provide a developer on the patterned photoresist material layer to remove the diffused regions to facilitate creating smaller features in the patterned photoresist;
   a fluorescence spectroscopy system having a light source operable to provide a light beam over a predetermined wavelength range at the photoresist material layer and a photodetector operable to receive an emitted light beam that provides a measurement signal indicative of the proportion of photoresist material remaining on the substrate due to the fluorescence of the photoresist material layer; and
   a control system operable to determine a critical dimension relating to resist structures formed on the photoresist material layer utilizing the measurement signal and compare the critical dimension to a desired critical dimension.

2. The system of claim 1, the control system adapted to repeat application of the trimming compound and the developer if the critical dimension is not within a certain criteria of the desired critical dimension.

3. The system of claim 1, the control system adapted to adjust at least one trimming component if the critical dimension is not within a certain criteria of the desired critical dimension.

4. The system of claim 3, the at least one trimming component being at least one of concentration, volume, pressure, temperature and diffusion time.

5. The system of claim 3, the adjusted trimming components being utilized in-situ.

6. The system of claim 3, the adjusted trimming components being utilized in the development of subsequent wafers and/or processes.

7. The system of claim 1, the photoresist material layer containing a polymer having an acid labile group that reacts with a cleaving compound to form one of an acidic and basic substance that is removable by a developer that is the other of an acidic and basic substance.

8. The system of claim 1, the trimming compound being a gas.

9. The system of claim 1, the trimming compound being a solution.

10. The system of claim 1, the critical dimension and the desired critical dimension being a thickness of a resist line structure.

11. The system of claim 1, the critical dimension and the desired critical dimension being a width between two resist line structures.

12. The system of claim 1, further comprising a signature library containing a plurality of signatures corresponding to critical dimension measurements and a signature generation system adapted to convert the measurement signal to a signature corresponding to a measured critical dimension for matching with signatures in the signature library.

13. The system of claim 1, the control system being adapted to locate a match in the signature library with the generated signature and determine the signature matching the generated signature is a signature corresponding to a desired critical dimension and repeating the application of the trimming compound and application of the developer if the desired critical dimension is not met.

14. The system of claim 1, the light source having a predetermined wavelength range being in the range of about 100 nm to about 800 nm.

15. The system of claim 1, the light source being a broadband light source.

16. The system of claim 1, the light source being coupled to a filter adapted to provide at least one excitation wavelength and the photodetector being coupled to a screening filter to provide an emitted light spectrum of wavelengths to the photodetector.

17. A method for facilitating smaller features in a patterned photoresist material layer, comprising:
   applying a trimming compound to a patterned photoresist material layer having a plurality of photoresist structures, the trimming compound diffusion into side and top portions of the plurality of photoresist structures to form diffused regions in the side and top portions of the plurality of photoresist structures;
   applying a developer to the patterned photoresist material layer to remove the diffused regions;
   transmitting a beam of light at the patterned photoresist material layer;
   detecting the fluorescence of the photoresist material layer by measuring an emitted beam of light from the photoresist material layer;
   determining a critical dimension corresponding to at least one of the plurality of photoresist structures based on the measured emitted beam of light; and
   comparing the critical dimension to a desired critical dimension.

18. The method of claim 17, further comprising repeating the application of the trimming compound and the developer until the critical dimension is within a certain criteria of the desired critical dimension.

19. The method of claim 17, further comprising adjusting at least one trimming component if the critical dimension is not within a certain criteria of the desired critical dimension.

20. The method of claim 19, the at least one trimming component being at least one of concentration, volume, pressure, temperature and diffusion time of the trimming compound.

21. The method of claim 19, the adjusting of the at least one trimming component being utilized in-situ.

22. The method of claim 19, the adjusting of the at least one trimming component being utilized in the development of subsequent wafers and/or processes.

23. The method of claim 17, the photoresist material layer containing a polymer having an acid labile group that reacts with a cleaving compound to form one of an acidic and basic substance that is removable by a developer that is the other of an acidic and basic substance.

24. The method of claim 17, the trimming compound being a gas.

25. The method of claim 17, the trimming compound being a solution.

26. The method of claim 17, further comprising generating a signature corresponding to a determined critical dimension and matching the signature with a plurality of signatures stored in a signature library corresponding to critical dimension measurements.

27. The method of claim 26, further comprising determining if the signature matching the generated signature is a signature corresponding to a desired critical dimension and repeating the application of the trimming compound and application of the developer if the desired critical dimension is not met.

28. A system for facilitating smaller features in a patterned photoresist material layer, comprising:
   means for applying a trimming compound to a patterned photoresist material layer having a plurality of photoresist structures, the trimming compound diffusion into side and top portions of the plurality of photoresist structures to form diffused regions;
   means for applying a developer to the patterned photoresist material layer to remove the diffused regions;
   means for transmitting a beam of light at the patterned photoresist material layer;
   means for detecting the fluorescence of the photoresist material layer by measuring an emitted beam of light from the photoresist material layer;
   means for determining a critical dimension corresponding to the plurality of photoresist structures based on the measured emitted beam of light; and
   means for comparing the critical dimension to a desired critical dimension.

* * * * *